United States Patent
Wang et al.

(10) Patent No.: US 8,047,055 B2
(45) Date of Patent: Nov. 1, 2011

(54) SIZE SEGREGATED AEROSOL MASS CONCENTRATION MEASUREMENT WITH INLET CONDITIONERS AND MULTIPLE DETECTORS

(75) Inventors: Xiaoliang Wang, Reno, NV (US); Jugal K. Agarwal, New Brighton, MN (US); George John Chancellor, Lindstrom, MN (US); James Evanstad, Mahtomedi, MN (US); Anthony E. Hase, White Bear Township, MN (US); Sreenath Avula, Vadnais Heights, MN (US); James E. Farnsworth, Shoreview, MN (US); David A. Lieder, Minneapolis, MN (US)

(73) Assignee: TSI, Incorporated, Shoreview, MN (US)

( * ) Notice: Subject to any disclaimer, the term of this patent is extended or adjusted under 35 U.S.C. 154(b) by 53 days.

(21) Appl. No.: 12/705,398

(22) Filed: Feb. 12, 2010

(65) Prior Publication Data

US 2010/0288921 A1 Nov. 18, 2010

Related U.S. Application Data

(63) Continuation-in-part of application No. 12/187,827, filed on Aug. 7, 2008, now Pat. No. 7,932,490.

(60) Provisional application No. 60/964,008, filed on Aug. 8, 2007, provisional application No. 61/152,084, filed on Feb. 12, 2009, provisional application No. 61/303,547, filed on Feb. 11, 2010.

(51) Int. Cl.
*B01D 59/44* (2006.01)
*G01N 21/00* (2006.01)
*B05C 1/00* (2006.01)

(52) U.S. Cl. .......... 73/28.01; 73/30.01; 73/335.01; 356/438; 356/336; 356/337; 250/299; 250/397; 250/287; 424/489

(58) Field of Classification Search .......... 250/287, 250/299, 397; 73/28.01, 30.01, 335.01; 356/438, 356/336, 337; 424/489
See application file for complete search history.

(56) References Cited

U.S. PATENT DOCUMENTS 6,674,529 B2 * 1/2004 Sachweh et al. .......... 356/338
(Continued)

FOREIGN PATENT DOCUMENTS

KR 10-1989-0702012 A 12/1989
(Continued)

OTHER PUBLICATIONS

International Preliminary Report on Patentability, dated Feb. 18, 2010.

*Primary Examiner* — Nikita Wells
(74) *Attorney, Agent, or Firm* — Patterson Thuente Christensen Pedersen, P.A.

(57) ABSTRACT

A system for measuring size segregated mass concentration of an aerosol. The system includes an electromagnetic radiation source with beam-shaping optics for generation of a beam of electromagnetic radiation, an inlet sample conditioner with adjustable cut-size that selects particles of a specific size range, and an inlet nozzle for passage of an aerosol flow stream. The aerosol flow stream contains particles intersecting the beam of electromagnetic radiation to define an interrogation volume, and scatters the electromagnetic radiation from the interrogation volume. The system also includes a detector for detection of the scattered electromagnetic radiation an integrated signal conditioner coupled to the detector and generating a photometric output, and a processor coupled with the conditioner for conversion of the photometric output and cut-size to a size segregated mass distribution.

34 Claims, 5 Drawing Sheets

U.S. PATENT DOCUMENTS

| | | | |
|---|---|---|---|
| 7,932,490 B2 * | 4/2011 | Wang et al. | 250/287 |
| 2002/0018204 A1 | 2/2002 | Sachweh | |
| 2008/0038363 A1 * | 2/2008 | Zaffaroni et al. | 424/502 |
| 2010/0181387 A1 * | 7/2010 | Zaffaroni et al. | 239/13 |

FOREIGN PATENT DOCUMENTS

| | | |
|---|---|---|
| KR | 10-0349174 B1 | 8/2002 |
| KR | 10-2005-0023339 A | 3/2005 |

* cited by examiner

US 8,047,055 B2

SIZE SEGREGATED AEROSOL MASS CONCENTRATION MEASUREMENT WITH INLET CONDITIONERS AND MULTIPLE DETECTORS

RELATED APPLICATIONS

The present application is a continuation-in-part and claims priority to U.S. patent application Ser. No. 12/187,827, filed Aug. 7, 2008, which claims the benefit of U.S. Provisional Application No. 60/964,008, filed Aug. 8, 2007, both of which are incorporated by reference herein in their entirety. This application further claims the benefit of the filing dates of U.S. Provisional Application No. 61/152,084, filed Feb. 12, 2009, and of U.S. Provisional Application No. 61/303,547, filed Feb. 12, 2010, both of which are incorporated by reference herein in their entirety.

FIELD OF THE INVENTION

The present disclosure relates generally to the detection of particles, and more specifically to the measurement of dust particle concentrations and size distributions.

BACKGROUND OF THE INVENTION

Human exposure to aerosols from indoor, outdoor, or workplace causes adverse health effects. The United States Environmental Protection Agency (EPA) promulgates regulations on PM10 (mass of particles with aerodynamic diameters less than approximately 10 μm) and PM2.5 (mass of particles with aerodynamic diameters less than approximately 2.5 μm). The American Conference of Governmental Industrial Hygienists (ACGIH) has also established regulations on respirable, thoracic and inhalable aerosols, defined as particles having aerodynamic diameters of less than 4 μm, 10 μm, and 100 μm respectively. A discussion of the various regulations are found at *National Primary and Secondary Ambient Air Quality Standards,* 40 Code of US Federal Regulation, Chapter 1, Part 50 (1997) and Vincent, J. H., *Particle Size-Selective Sampling for Particulate Air Contaminants* Cincinnati, ACGIH (1999), both of which are hereby incorporated by reference except for explicit definitions contained therein.

Presently, the federal reference method (FRM), which utilizes filter samplers, is implemented to determine compliance with mass based air quality standards. The particle size collected by the filter samplers is determined by a size selective inlet. Typically, the filter method requires a relatively long sampling time, about 24 hours, to collect enough mass on the filter, with the results not being available until the samples are analyzed in the laboratory.

Direct-reading instruments provide near real-time measurement of aerosol mass concentrations. For example, a photometer can be calibrated to surrogate fine particle mass concentration over a wide concentration range. But it does not provide size information. On the other hand, an optical particle counter (OPC) or aerodynamic particle sizer (APS) may provide very high resolution size distributions. But these instruments only work at relatively low concentrations due to coincidence errors.

U.S. Patent Publication Number US 20090039249A1 (U.S. patent application Ser. No. 12/187,287) commonly assigned to the assignee of the present invention, and to which the present application claims priority, discloses an invention that combines photometry and optical or aerodynamic particle sizing in one optical device for measuring size segregated mass concentrations, for example, PM10, PM2.5 and PM1, or inhalable, thoracic and respirable fractions, in real time. The optical device features a single optical chamber and a single detector. Such a design reduces instrument components and simplifies the instrument configurations. However, such a design may pose challenges to measuring very low concentrations using photometric signals.

Optical or aerodynamic sizing requires highly focused light beam(s) to produce a strong scattering pulse. To achieve a highly focused light beam, optics having shorter focal lengths are typically employed. Such optics have wide convergence/divergence angles, thus bathing larger surface areas. For example, optics and light traps can create a large amount of stray light, and cause great difficulties to design apparatuses, for example apertures, in reducing stray light. Because the photometric signal is detected by the same detector in the same optics chamber, the stray light causes low signal-to-noise levels of the photometric measurement at very low concentrations, for example, at concentrations in the range of 0.1-1 μg/m$^3$. The stray light also causes background photometric signal drift at different environment temperatures.

SUMMARY OF THE INVENTION

Embodiments of the claimed invention achieve real-time size segregated mass concentration measurement over a wide concentration range. The difficulties related to the combined photometry and optical/aerodynamic sizing due to a single detector and/or a single optical chamber are significantly reduced in some embodiments, while at the same time, measurement accuracy is improved.

Various embodiments of the invention include a hybrid apparatus and/or method for determining the particle size distribution and mass distributions in the particle size range of interest (collectively referred to herein as size segregated aerosol mass concentration) and in real time. The disclosed device may have multiple detectors, radiation sources with multiple wavelengths or multiple optics chambers. A cut-size adjustable sample conditioner may be applied to the inlet of the device. This device may provide a simultaneous and real time indication of the size segregated mass concentration of the interrogated particle stream. The measurement may be performed on particles suspended in a medium such as a liquid, a gas or some combination thereof When the medium is a gas, the product is known as an aerosol. The gas may be air, nitrogen, argon, helium, carbon dioxide or any other gas or gas mixtures. Particles can be solid, liquid or a combination of both.

Structurally, certain embodiments of the invention implement incident beams of electromagnetic radiation (hereinafter "light beam") that define interrogation volumes through which a suspended particle stream passes. A portion of the light that is scattered from the interrogation volumes by the particles may be sensed by detectors. In some embodiments, the detectors generate an electrical signal proportional to the scattered light received from particles. The electrical signal may be processed by one or multiple signal conditioning circuits, including: (1) an integrated photometric signal proportional to the intensity of incident light that is scattered by the particle or ensemble of particles in the interrogation volume and intercepted by the detector; (2) a pulse height signal derived from scattered light originating from individual particles; and (3) a time-of-flight signal providing a direct or indirect measurement of the particle velocity through the interrogation volume region. The integrated signal may comprise a biased or time-averaged signal that can be correlated to particle mass concentration, especially if the particles within the interrogation volume are made of primarily fine or respirable particles. The pulse height signal may be indicative of the particle optical equivalent size. The time-of-flight signal may be indicative of the particle aerodynamic diameter. Given the properties of the particles (e.g. shape, refractive index, density), the mass concentration may be inferred from the particle size distribution. The mass concentration can be obtained by performing mathematical operations on the detected signals, from which the size segregated mass fractions such as PM1, PM2.5, PM10, inhalable, thoracic and respirable may be obtained.

Some embodiments of the invention measure size segregated mass concentrations using a single optical chamber and a single detector with a cut-size adjustable inlet conditioner. The inlet conditioner may be controlled to allow only particles of a certain size range to enter the integration volume at a time. The optical system may be optimized for detecting the total light scattering from all particles in the integration volume. The integrated photometric signal generated from total light scattering may be correlated to aerosol mass concentration. The size segregated mass concentration may be inferred by scanning the two or more mass fractions through the inlet conditioner.

Some embodiments of the invention measure size segregated mass concentrations using a single optical chamber and multiple detectors. Each detector may be optimized for one kind of optical signal. For example, one detector may be optimized for the integrated photometric signal, and one for the pulse height or time-of-flight signal.

Some embodiments of the invention measure size segregated mass concentrations with multiple optics chambers, each optimized for one kind of signal. For example, one chamber optimized for measuring the integrated photometric signal, and the other optimized for the pulse height or time-of-flight signal. These chambers could be in one instrument or in multiple instruments that are connected electrically.

Some embodiments of the invention measure size segregated mass concentrations with multiple optics chambers that only measure the integrated photometric signal. Each chamber is equipped with an inlet sample conditioner that selects particles of a certain size range to enter the integration volume.

Some embodiments of the invention improve the measurement accuracy and extend the particle size range with multiple radiation sources with different wavelengths. Since the light scattering sensitivity depends on the wavelength of the illuminating radiation. A shorter wavelength may be optimized for measuring smaller particles, while a longer wavelength may be optimized for larger particles.

A representative and non-limiting sensitive size range for the various embodiments of the invention is from 0.1 µm to 20 µm. A non-limiting dynamic range of particle mass concentration is 0.0001 to 400 mg/m$^3$. Certain embodiments may include an optional filter installed downstream of the optical chamber to collect particles for direct mass measurement. Other appurtenances include devices for controlling parameters such as light power and flow.

Some embodiments of this invention describe devices and methods that improve the instrument operation reliability, measurement accuracy and ease of use. Examples include an integrated touch screen for a user interface, an internal algorithm to determine a conversion from light scattering pulse height to aerodynamic particle diameter, and an Ethernet connection for instrument communication.

BRIEF DESCRIPTION OF THE DRAWINGS

The invention may be more completely understood in consideration of the following detailed description of various embodiments of the invention in connection with the accompanying drawings, in which.

Figure 1:
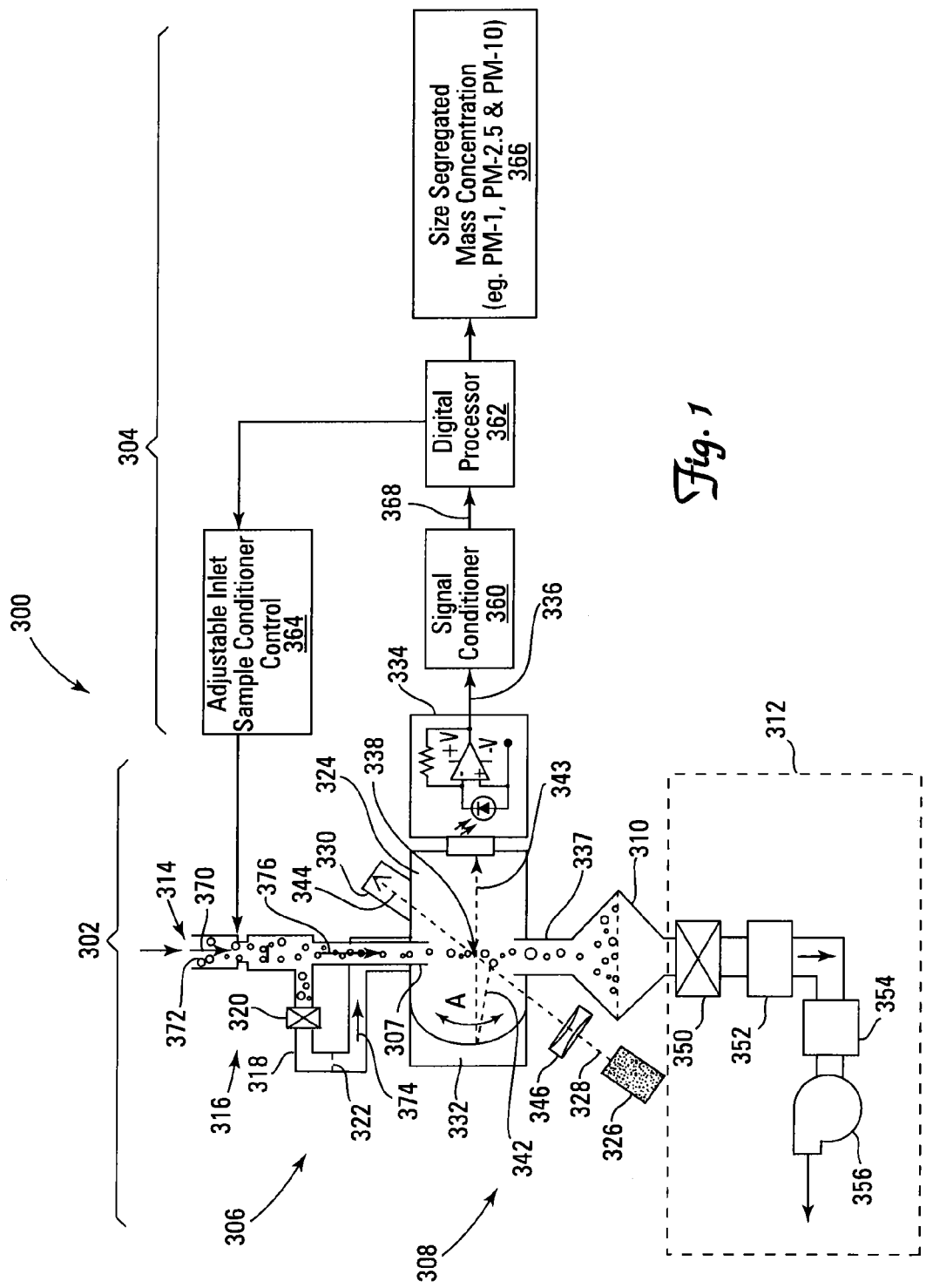
FIG. 1 is a schematic diagram of a size segregated mass concentration measuring device having a single optical chamber, single integrated photometric detector, and using a cut-size adjustable inlet sample conditioner to control the particle size entering the optical chamber, according to an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

Referring to FIG. 1, a schematic diagram of adjustable cut-size segregated mass concentration measurement system 300 is depicted in an embodiment of the invention. System 300 includes adjustable cut-size aerosol measurement section 302 coupled to a control system, such as signal acquisition and processing system (SAPS) 304.

Aerosol measurement section 302 includes an adjustable inlet portion 306, detection portion 308, optional filter 310, and pumping system 312. Adjustable inlet portion 306 and pumping system 312 are operably coupled to detection portion 308, with pumping system 312 coupled through outlet filter 310.

In the embodiment depicted in FIG. 1, adjustable inlet portion 306 includes inlet 314 coupled to adjustable cut-size inlet sample conditioner 316. Adjustable inlet portion 306 may include a sheath flow conditioning loop 318 having a filtration device 320 and flow controlling and measuring device 322. In one embodiment, flow controlling and measuring device 322 may comprise an orifice.

Adjustable cut-size inlet sample conditioner 316 may include, but not be limited to the following forms: (1) an impactor with adjustable cut-size, through, for example, scanning flowrate or changing nozzle size; (2) a cyclone with adjustable cut-size, through, for example, scanning flowrate or changing physical dimensions; (3) a rotating device, for example, a fan, with adjustable speed. Adjustable cut-size inlet sample conditioner 316 may also include an inlet cut-size controller 364 as discussed below in further detail.

Detection portion 308 includes optics chamber 324, light source 326 emitting light beam 328, light trap 330, light collecting optics 332, light detector 334 with light detector output signal 336, and outlet nozzle 337. Optics chamber 324 defines viewing or interrogation volume 338. Light beam 328 may include scattered portion 342 and unscattered portion 344. Scattered portion 342 includes collected scattered light 343 incident on light detector 334. Light detector 334 may comprise any number of known detectors, including a photodiode or a photomultiplier tube.

Detector portion 308 and light detector 334 may be adapted or optimized (e.g. detector type, sensitivity range, location, etc.) to detect a particular particle or light characteristic, including overall intensity of scattered light 343, pulse-height, time-of-flight (pulse width) or other such characteristics. In other embodiments, detector portion 308 may be adapted to detect light emitted from the particles as a result of the intersection of light beam 328 and the particles. In the embodiment depicted, detector portion 308 and light detector 334 are adapted to detect and determine scattered light intensity.

Light source 326 and emitting light beam 328, may be electromagnetic radiation sources such as a diode laser, an LED or a lamp (broadband or line emitting), or other similar light source.

Detection portion 308 may also include optional beam-shaping optics 346 that may include a lens such as a cylindrical lens. The shaping optics may additionally or alternatively comprise reflective components such as mirrors, or fiber optic components (not depicted). Filter 310 in one embodiment may comprise a gravimetric filter 310 coupled to outlet nozzle 337 of detection portion 308. Filter 310 is in turn operably coupled to pump system 312. In other embodiments, filter 310 may not be present in system 300, such that pumping system 312 is coupled directly to outlet nozzle 337.

As depicted in the embodiment of FIG. 1, pumping system 312 includes protection filter 350, flowmeter 352, flow pulsation damping chamber 354 and pump or blower 356 that may be ducted to an exhaust. Numerous kinds of pumps or blowers 356 may be utilized, including, but not limited to, a diaphragm pump, a rotary vane pump, a piston pump, a roots pump, a linear pump or a regenerative blower.

Still referring to FIG. 1, control system SAPS 304 in one embodiment includes signal conditioner 360, processor 362, adjustable inlet sample conditioner controller 364, and output device 366.

Signal conditioner 360 may include hardware, such as a signal conditioning circuit, and software to condition light detector output signal 336, and deliver one or more conditioned signals 368. Processor 362 may comprise a digital microprocessor, microcontroller, or similar processing device, and may also include memory for storing data, algorithms, instructions, or other information.

Output device 366 may comprise data representing size segregated mass concentration and optionally may include devices for displaying and/or storing such data, such as display, a storage device, analog output or a computer.

In operation, an incoming flow stream 370 comprising particles 372 may be drawn through inlet 314 and passed through inlet sample conditioner 316. Inlet sample conditioner 316 may only allow particles 372 of a given size range to get through, and the penetration size range may be adjusted during the course of measurement, either manually, by controller 364, or a combination thereof.

Flow stream 370 may then be split into a sheath flow stream 374 and an aerosol flow stream 376. Sheath flow stream 374 may be diverted to sheath flow conditioning loop 318 and through filtration device 320 and flow measuring device 322.

Aerosol flow stream 376 passes through an inlet nozzle 307 to optics chamber 324 and viewing or interrogation volume 338. Interrogation volume 338 may be defined by the intersection of light beam 328 and aerosol flow stream 376.

As discussed above, size segregated mass concentration measurement system 300 may further comprise beam-shaping optics 346 that may include a lens such as a cylindrical lens. Beam-shaping optics 346 shape or focus light beam 328 prior to, or at, entry into optics chamber 324.

Within optics chamber 324, light beam 328 is scattered by particles 372 forming scattered portion 342 and unscattered portion 344. Scattered portion 342 dispersed at a solid angle A may be subtended by light collection system 332 or radiation collector (e.g. a spherical mirror, aspheric condenser lenses, or other electromagnetic radiation collection devices available to the artisan) within optics chamber 324. The angle A from which scattered light 342 is collected may be in the range of 0 degrees to 360 degrees. Unscattered portion 344 of light beam 328 may be captured by light trap 330.

Inner surfaces of optics chamber 324 may be coated with a black or high absorptivity coating such as an anodized coating. Collected light 343 gathered by light collecting system 332 may be transferred to detector 334. Light detector 334 may produce an electrical signal 336 proportional to the convolution of the incident electromagnetic radiation and the spectral sensitivity of detector 334.

In some embodiments, aerosol flow stream 376 exits optics chamber 324 through outlet nozzle 337 and may be passed through filter 310, which may be weighed to obtain mass concentration or be analyzed for chemical composition. Aerosol flow stream 376 may be drawn through optics chamber 324 by pumping system 312.

Signal conditioner 360, which in one embodiment is an integrated photometric signal conditioning circuit, generates integrated outputs 368 proportional to intensity, or watt density of the collected light gathered by the radiation collector and incident on the detector 334. The outputs are in turn proportional to the light flux scattered from all the particles classified by the inlet sample conditioner in the interrogation volume region. The outputs may be routed to processor 362 for analysis. This information is combined with the inlet conditioner 316 known particle cut-size to calculate size segregated mass concentration distributions. The result can be output to output device 366, for display, storage, transfer, or other use.

Figure 2:
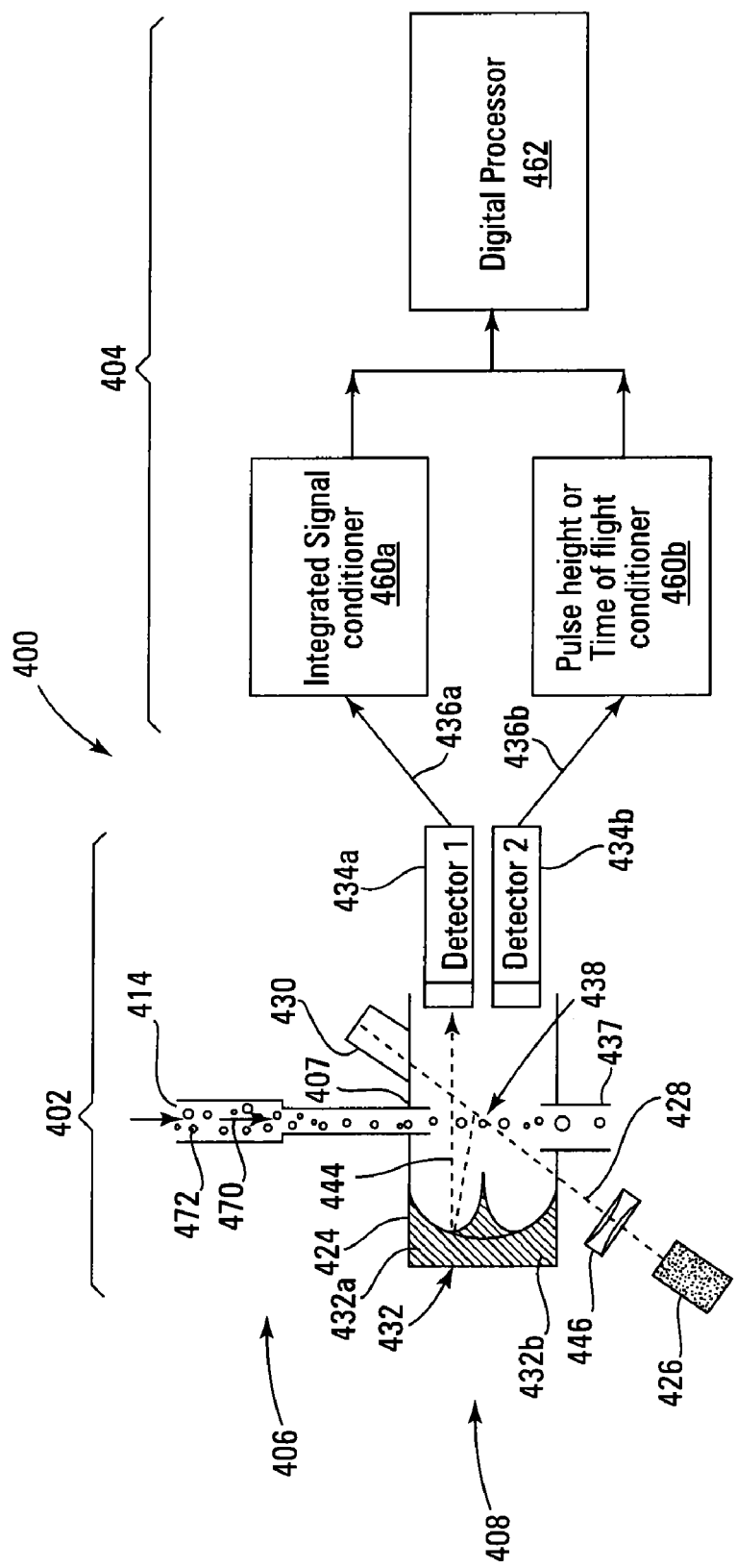
FIG. 2 is a schematic diagram of a size segregated mass concentration measurement device having a single optical chamber and multiple, specific-signal optimized detectors, according to an embodiment of the invention.

Referring to FIG. 2, size segregated mass concentration measurement system 400 differs from system 300 with respect to both aerosol inlet and particle detection. System 400 includes aerosol measurement section 402 coupled to a control system, such as SAPS 404.

Aerosol measurement section 402 includes an inlet portion 406 and detection portion 408. Although not depicted, it will be understood that inlet portion 406 may also include sheath flow, and aerosol measurement section 402 may also include optional filter 310, and pumping system 312 as previously depicted and described with reference to system 300 and FIG. 1. Inlet portion 406 and pumping system 312 are operably coupled to detection portion 408, with pumping system 312 optionally coupled through outlet filter 310.

In the embodiment depicted in FIG. 2, detection portion 408 includes optics chamber 424, light source 456 emitting light beam 428, light trap 430, light collecting optics 432, light detectors 434a and 434b with respective light detector output signals 436a and 436b, and outlet nozzle 437.

Although only two detectors are depicted, it will be understood that more than two detectors may be used.

It is also understood that the collection optics 432 may have multiple components, such as depicted 432a and 432b, each positioned to collect scattered light at optimal angles. In other embodiments, collecting optics 432 is substantially similar to collecting optics 332 of system 300.

Light detection portion 408, including light detectors 434a and 434b may be especially adapted to respectively detect one or more particular characteristics of the particles or scattered portion 442 of light beam 428. Such characteristics include intensity of scattered light 343, light pulse-height, time-of-flight (pulse width) or other such characteristics. It will be understood that a "pulse" generally refers to a pulse of scattered light as measured by light detector 434, and having a peak measured value, or pulse height, typically measured in volts, over a period of time, the pulse width.

Detector portion 408 and light detectors 434 may be adapted or optimized in a number of different ways. For example, a detector 434 may be designed to specifically detect and measure pulses, including either pulse height, width, measure particular wavelengths, or to have a particular sensitivity range. In other embodiments, a detector 434 may be located or positioned in a particular way to detect and measure a particular characteristic. In other embodiments, detector portion 408 and a detector 434 may be adapted to detect light fluoresced from the particles as a result of the intersection of light beam 328 and the particles.

In other embodiments, detector 434a may be combined with one component of the collecting optics 432 to collect more forward-scattering light, which yields a more sensitive integrated photometric signal. On the other hand, the detector 434b may be combined as one component of the collecting optics 432 to collect scattered light in a wide-angle range, so that the pulse height signal is a more monotonic and smooth function of particle size. Furthermore, a slower detector 434a may be used to average the integrated photometric signal, while a faster detector 434b may be used for pulse height or time-of-flight measurement.

In the embodiment depicted, light detector 434a is adapted to detect scattered light in a manner most conducive to determining light intensity. Light detector 434b is adapted to measure either pulse height or time of flight (pulse width). In another embodiment, a third light detector may be used, the third detector 434 measuring a third characteristic. Any individual characteristic, or a combination of these characteristics, may be used by the control system, SAPS 404, to determine mass concentration by size.

Optics chamber 424 defines viewing or interrogation volume 438. Light beam 428 may include scattered portion 442 and unscattered portion 444. Scattered portion 442 includes collected scattered light 443 incident on light detectors 434a and 434b. Light detectors 434a and 434b may comprise any number of known detectors, including a photodiode or a photomultiplier tube.

Light source 456 emitting light beam 428 may be an electromagnetic radiation source such as a diode laser, an LED or a lamp (broadband or line-emitting), or other similar light source.

Detection portion 408 may also include optional beam-shaping optics 446 that may include a lens such as a cylindrical lens. The shaping optics may additionally or alternatively comprise reflective components such as mirrors, or fiber optic components (not depicted).

As depicted in FIG. 2, the control system comprises SAPS 404, which includes two or more conditioners 460. Each of the conditioners 460 may be adapted to condition a signal from a detector 434 associated with a particular characteristic. In the depicted embodiment, signal conditioner 460a is adapted to condition a signal from detector 434a for determining intensity. Conditioner 460a is communicatively coupled to detector 434a and receives signal 436a. Signal conditioner 460b is either adapted to condition a pulse height or time-of-flight signal 436b from detector 434b. In other embodiments, SAPS 404 includes three or more conditioners 460. For example, SAPS 404 may include an integrated signal conditioner, pulse height conditioner, coupled to time of flight conditioner, and their respective detectors 434.

SAPS 404 also includes processor 462, and though not depicted in FIG. 2, it will be understood that SAPS 404 may also generally include an output device 366 communicatively coupled to processor 462.

Similar to system 300 described above, in operation an incoming flow stream 470 comprising particles 472 may be drawn through inlet 414. However, in this embodiment, incoming flow stream 470 is not conditioned by passing through an adjustable inlet sample conditioner.

Flow stream 470 passes through inlet nozzle 437 to optics chamber 424 and viewing or interrogation volume 438. Beam-shaping optics 446 may shape or focus light beam 428 prior to, or at, entry into optics chamber 424.

Within optics chamber 424, light beam 428 is scattered by particles 472 forming scattered portion 442 and unscattered portion 444. Scattered portion 442 is dispersed at a solid angle A and may be subtended by light collection system 432 or radiation collectors within optics chamber 424. The angle A from which scattered light is collected may be in the range of 0 degrees to 360 degrees. Unscattered portion 444 of light beam 428 may be captured by light trap 430.

In this embodiment, pulse height or time-of-flight conditioner 460b provides a signal representative of optical or aerodynamic particle size distribution, which is combined with the integrated photometric signal 460a at processor 462 to produce size segregated mass distribution.

As an alternative to, or in addition to, either the pulse height measurement or the time-of-flight measurement, the pulse height and pulse width can be multiplied or integrated in a convolution integral by processor 462 to produce an "area" measurement of the signal pulse. The area product can be used to infer particle size. Herein, "area" is generally considered to be some product of the pulse width and the pulse height. In one embodiment, "area" is the pulse height multiplied by the pulse width. In another embodiment, "area" is determined by digitizing the pulse with sufficient resolution to perform a numerical integration of the pulse signal over the duration of the pulse. The errors associated with particle sizing when using pulse measurement techniques can be reduced by using pulse area to size particles instead of using pulse height or amplitude. See U.S. Provisional Patent Application No. 61/303,547 to Farnsworth et al., assigned to the assignee of the present application, the disclosure of which is included in Appendix A and which is incorporated by reference herein in its entirety except for express definitions therein.

For a particle of a given size, the pulse height or amplitude produced by the particle will typically be at a maximum when the trajectory is through the center of the measurement volume. Conversely, the pulse width produced by such a particle will typically be maximized near the edges of the measurement volume. The pulse area profile produced by a given particle is less dependent on the trajectory through the interrogation volume than either the pulse height or the time-of-flight components that make up the pulse area indication. Accordingly, a product (i.e. area) of the two profiles yields a profile more uniform (less sensitive to the position within the measurement volume) than either of its components. Sizing based on pulse area allows the designer to counterbalance these two profiles, resulting in a more uniform size measurement throughout the measurement volume.

Size measurement by pulse height can place a limit on the size of the particle that can be measured. The limit is determined by the output limit of the detector circuit. If a particle scatters enough light to rail the detector circuit, the peak of the pulse signal will be "clipped." Pulse width, on the other hand, will continue to increase regardless of whether the detector signal is clipped, thus extending the size range of a pulse area measurement. Therefore, the effects of the limit on pulse height measurements are mitigated by using pulse area to size particle.

It is noted that area-based signal processing is known to improve OPC size resolution, but the prevailing belief is that the velocity profile across the nozzle must be uniform for the area measurement to have any value. See Aerosol Measurement, $2^{nd}$ ed. (2001) edited by Baron and Willeke, pg 438, the disclosure of which are hereby incorporated by reference except for definitions expressly defined therein. Accordingly, existing devices utilize sheath flows to accomplish uniform velocity profiles.

Because of the inverse relationship between the particle velocity and beam intensity profiles, the pulse area technique disclosed herein provides sufficient accuracy and resolution without the use of sheath flows, and can extend the dynamic range of pulse measurement techniques generally.

Therefore, by using detectors 434 and conditioners 460 adapted to detect and condition specific characteristics, system 400 improves the measurement accuracy, and extends the measurement size and concentration range, as compared to single detector-conditioner systems.

Figure 3:
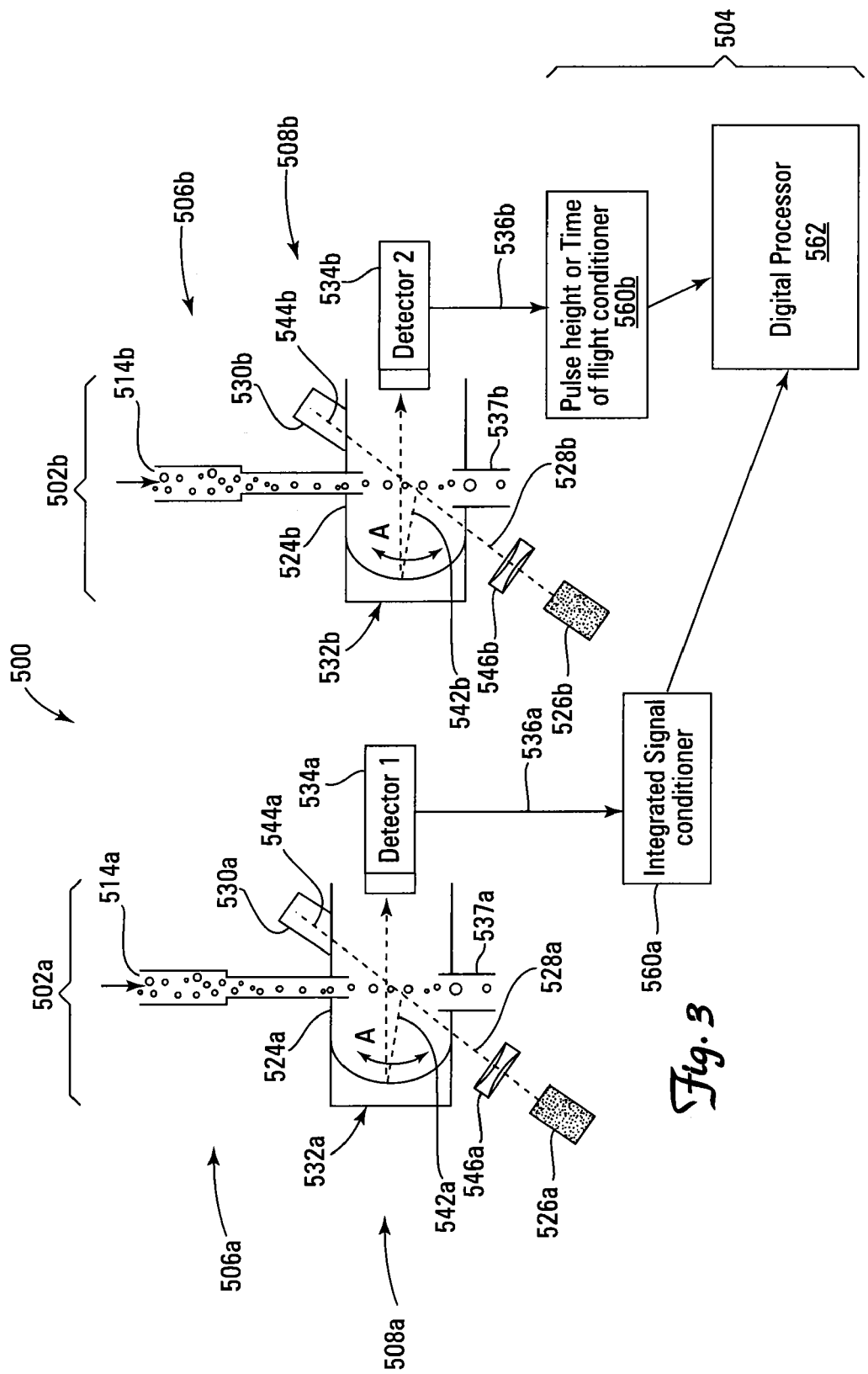
FIG. 3 is a schematic diagram of a size segregated mass concentration measurement device having multiple optical chambers, each optimized for a specific kind of signal, according to an embodiment of the invention.

Referring to FIG. 3, system 500 having multiple optical chambers is depicted in an embodiment of the invention. System 500 includes two aerosol measurement sections 502a and 502b, coupled to a control system, which in one embodiment is a single SAPS 504. It will be understood that in other embodiments, system 500 may include more than two sections 502.

Each aerosol measurement section 502 includes an inlet portion 506 and detection portion 508. Although not depicted, it will be understood that each inlet portion 506 may have sheath flow 318, each aerosol measurement section 502 may also include optional filter 310, and pumping system 312 as previously depicted and described with reference to system 300 and FIG. 1. Inlet portions 506 and pumping systems 312 are operably coupled to detection portions 508, with pumping systems 312 optionally coupled through outlet filters 310. In other embodiments, a single filter 310 and pumping system 312 may serve multiple aerosol measurement sections 502.

Each detection portion 508 includes an optics chamber 524, light source 526 emitting light beam 528, light trap 530, light collecting optics 532, light detectors 534 with light detector output signal 536, and outlet nozzle 437.

Detection portions 508a and 508b, and their respective detectors 534a and 534b, may be especially adapted to detect a particular characteristic of scattered portion 442 of light beam 428. Similar to the detection portions 408 and detectors 434 described above, detection portions 508a and 508b may be adapted or optimized to detect a particular characteristic such as light intensity, pulse height, time-of-flight (pulse width) or another such characteristic.

In the depicted embodiment, detection portion 508a includes a single chamber 524a with detector 534a and integrated signal conditioner 560a especially adapted and optimized to condition and output a signal 568a for determining a first characteristic, in this case, intensity, of scatter portion 442 of light. Detection portion 508b includes a single chamber 524b with detector 534b adapted to detect a second characteristic, in this case either pulse height and/or time-of-flight, and conditioner 560b, which is adapted to condition signal 536a and output representative of the second characteristic, in this case, pulse height or time-of-flight signal 568b.

As in other embodiments, light sources 526 emitting light beams 528 may be electromagnetic radiation sources such as diode lasers, LEDs, lamps (broadband or line emitting), or other similar light sources. Detection portion 508 may also include optional beam-shaping optics 546 that may include lenses. The shaping optics may additionally or alternatively comprise reflective components such as mirrors, or fiber optic components (not depicted).

Conditioners 560a and 560b are each communicatively coupled to a single processor 562, though in other embodiments, multiple processors may be used. System 500 operates similarly to the previously described embodiments, though one optical chamber may be optimized to measure a first characteristic, such as the integrated signal, and the other(s) may be optimized to measure a second characteristic, such as pulse height or time-of-flight. Such a design eliminates the difficulties of trying to measure two characteristics such as integrated signal and pulse height or time-of-flight in one optical chamber with a common detector, where reducing background light scattering is very difficult due to the short focal length needed to generate high intensity light beams for particle pulse measurement. Using multiple optical chambers introduces flexibilities in optimizing each chamber for one type of signal, thus greatly improving measurement accuracy, and extending size and concentration range. Each measurement chamber may or may not share peripheral components, such as inlet, filters, flowmeter and pump.

Figure 4:
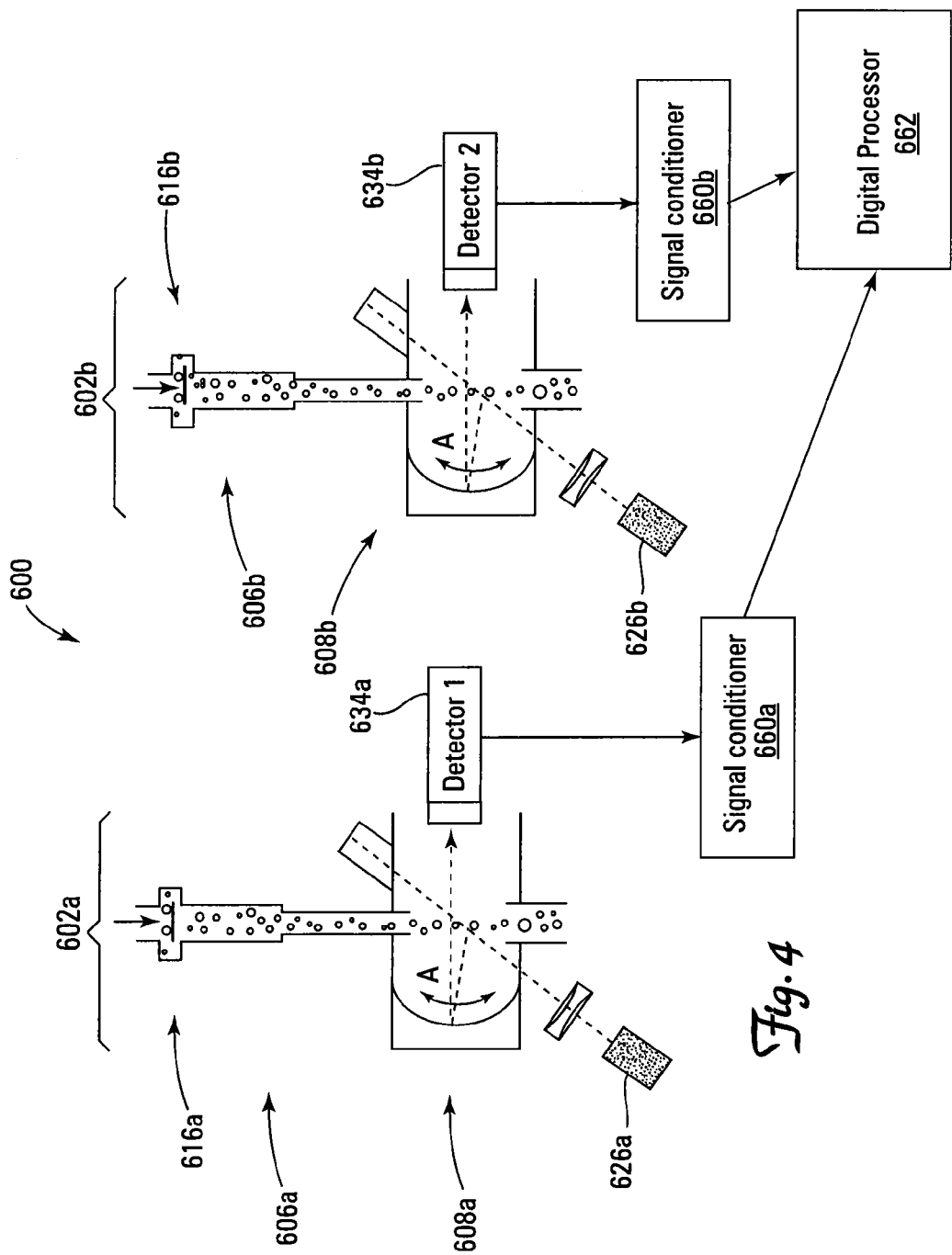
FIG. 4 is a schematic diagram of a size segregated mass concentration measurement device having multiple inlet conditioners and multiple optical chambers, according to an embodiment of the invention.

Referring to FIG. 4, system 600 with multiple optical chambers, each equipped with an inlet sample conditioner, is depicted in an embodiment of the invention. System 600 includes two or more aerosol measurement sections 602 and a control system, SAPS 604. SAPS 604 includes two or more signal conditioners 660 corresponding to the two or more aerosol measurement sections 602 communicatively coupled to digital processor 662.

Each inlet portion 606 includes an inlet sample conditioner 616. Inlet sample conditioner 616a is adapted to restrict the range of allowed particle size to a predefined particle size or range, while inlet sample conditioner 616b is adapted to restrict particle sizes to a second, different, predefined particle size or range. Inlet conditioners 616 may be, but are not limited to, impactors, cyclones, virtual impactors or virtual cyclones.

It will be understood that each detection portion 608 includes substantially the same components as previously described detection portions 508, operating in a similar manner. However, unlike system 500, because inlet portions 616 are adapted to restrict particle size, each detection portion 608 may only detect or measure the integrated photometric signal of the particle size selected by its respective inlet sample conditioner 616. Results from each aerosol measurement system 602 may be combined to produce size segregated mass distribution via conditioners 660 and processor 662.

The advantages of the design of system 600 are that (1) background light reduction difficulties are avoided when a single chamber was used for both integrated signal and single particle sizing; (2) improved flexibility in optics design; (3) since each chamber detects a photometric signal, they may use very similar or common hardware and firmware for signal processing, as well as a common algorithm for calculating mass distributions.

Figure 5:
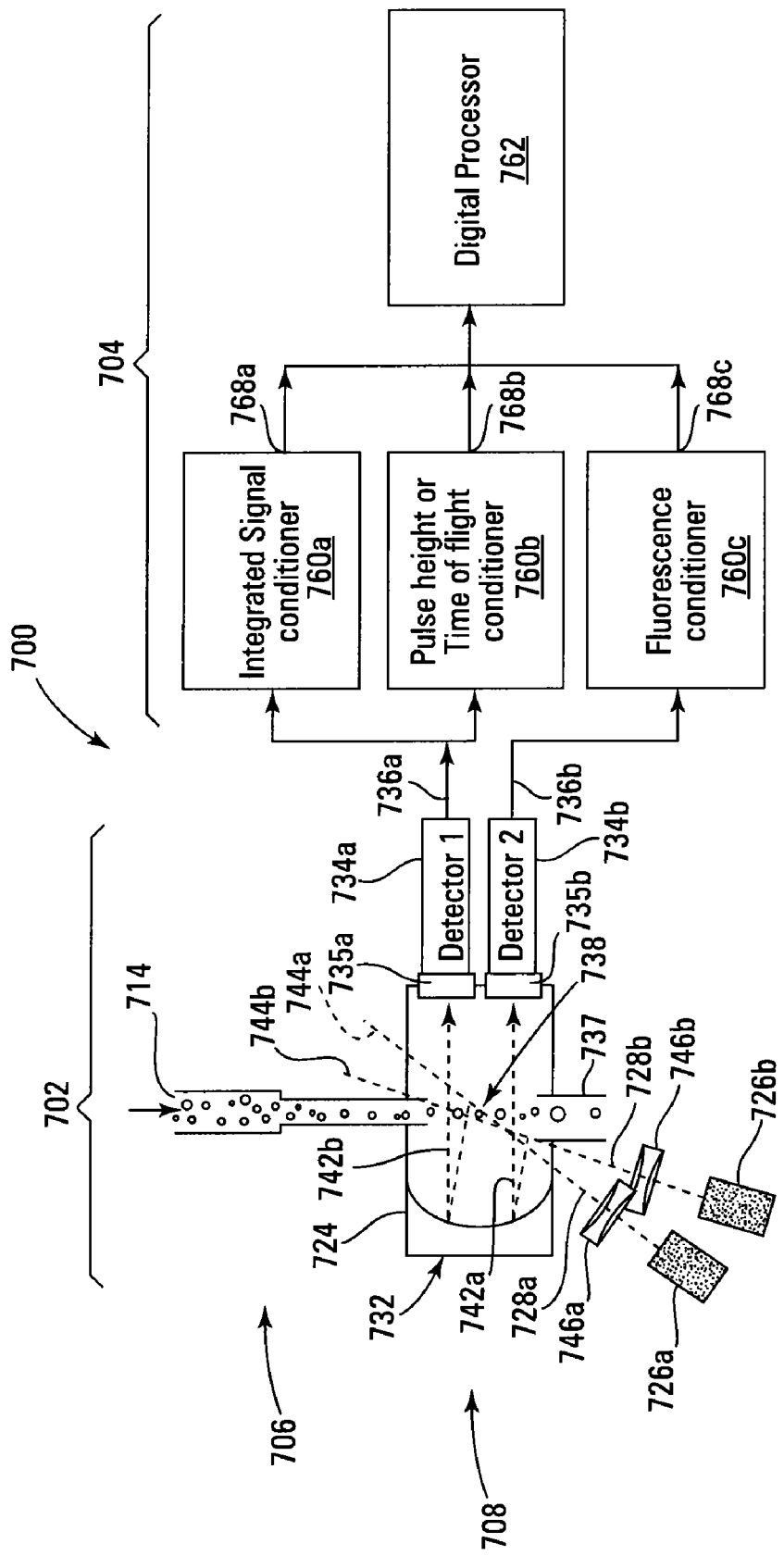
FIG. 5 is a schematic diagram of a size segregated mass concentration measurement utilizing radiation sources of multiple wavelengths, according to an embodiment of the invention.

Referring to FIG. 5, a dual wavelength system 700 is depicted in an embodiment of the invention. The dual wavelength system 700 includes a single optical chamber and two light emission sources that propagate light beams with different wavelengths. System 700 includes aerosol measurement section 702 coupled to a control system, which in the depicted embodiment is SAPS 704.

Aerosol measurement section 702 includes an inlet portion 706 and detection portion 708. Although not depicted, it will be understood that inlet portion 706 may have a sheath flow conditioning loop 318, and aerosol measurement section 702 may also include optional filter 310, and pumping system 112 as previously depicted and described with reference to system 300 and FIG. 1. Inlet portion 706 and pumping system 312 are operably coupled to detection portion 708, with pumping system 112 optionally coupled through outlet filter 310.

Detection portion 708 includes optics chamber 724, light sources 726a and 726b emitting light beams 728a and 728b, respectively, optional light traps 730 (not depicted), light collecting optics 732, light detectors 734a and 734b with respective light detector output signals 736a and 736b, and outlet nozzle 737. Light detectors 734a and 734b may be fitted with band pass filters 735a and 735b, respectively, and each light detector 734a and 734b may be especially adapted to detect a particular characteristic of scattered portion 742 of the respective light beams 728a and 728b. Light sources 756 emitting light beams 728 may be electromagnetic radiation sources such as diode lasers, LEDs, lamps (broadband or line emitting), or other similar light sources.

Optics chamber 724 defines viewing or interrogation volume 738. Detection portion 708 may also include optional beam-shaping optics 746 that may include a lens such as a cylindrical lens, similar to those described above.

SAPS 704 include multiple conditioners 760, receiving multiple light detector output signals 736. In the embodiment depicted, conditioners 760 include integrated signal conditioner 760a communicatively coupled to detector 734a and receiving signals 736a, and optimal pulse height or time of flight conditioner 760b communicatively coupled to detectors 734a and receiving signals 736a. Fluorescence conditioner 760c is communicatively coupled to detector 734b and receiving signals 736b.

SAPS 704 can also include processor 762, and though not depicted in FIG. 5, it will be understood that SAP 704 also generally includes an output device 766, similar to those described above, communicatively coupled to processor 762.

In one embodiment, the light sources 726a and 726b may be selected to include wavelengths of emission that capitalize on certain characteristics of the aerosol. For example, light source 726a may be selected to emit a wavelength that enhances the range of particles that can be detected in a scattering arrangement, such as discussed previously. Light source 726b, meanwhile, may be selected to include a wavelength or band pass known to fluoresce certain particles that are in the aerosol. See, e.g., U.S. Pat. No. 6,831,279 to Ho, which is hereby incorporated by reference in its entirety except for express definitions therein.

In operation, such an embodiment may utilize band pass filter 735a to detect the scattering wavelength emitted by light source 726a while blocking out the other wavelengths present in optics chamber 724 (e.g., wavelengths of light source 726b and attendant fluorescence wavelengths). Likewise, filter 735b can be utilized and selected to detect the fluorescence wavelength of the certain particles in the aerosol known to fluoresce while blocking out non-fluorescence wavelengths present in chamber 724 (e.g., wavelengths of lights sources 726a and 726b).

In another embodiment, the wavelengths of both lights sources 726a and 726b may be selected for scattering. The aerosol scattering response is a function of light wavelength. Typically shorter wavelengths produce more sensitive measurement for smaller particles, and longer wavelengths produce better measurement for larger particles. Using multiple wavelengths may improve the measurement accuracy, and extend the particle size range. Scattering signals from multiple wavelengths may yield extra information about particle properties, such as shape and refractive index. Further, particles originating from living organisms and biogenetic species may generate fluorescence patterns when illuminated by light with short wavelengths. Therefore, in addition to increasing measurement accuracy, by examining the fluorescence patterns of particles, bio-origin particles may be identified.

With respect to systems 300 to 700 described above, those embodiments involving measuring pulse height for particle sizing may have an internal algorithm stored in their respective control systems to determine a conversion from pulse height or optical size to aerodynamic size, employing one or multiple aerodynamic classifiers (eg. impactors or cyclones). This innovation guides a user through taking pulse height distribution with and without the aerodynamic classifiers. Finding the pulse height corresponding to 50% penetration of the aerosol being tested, and comparing that to known aerodynamic cut-size of the classifier allows the instruments firmware to calculate a conversion function. This allows pulse height size data to be converted internally to aerodynamic size. In some known devices, some OPC manufactures have documented procedures that will allow this factor to be determined externally and the applied to convert the data after it has been taken, which is an inferior process.

Additionally, embodiments described above may include an integrated touch-screen as a user interface. The touch-screen allows users to easily interact with the system, giving it functionality approaching the ease of use of a computer interface. Known photometers typically comprise membrane buttons. In some embodiments, output device 366 may comprise an interactive touch-screen display.

Systems 300 to 700 described above may also allow Ethernet communication. Such innovation allows setting a network of instruments. Each instrument may be assigned a unique IP address. A single computer may communicate to a large number of instruments, sending commands or downloading data. In prior art instruments, non-Ethernet protocols (e.g. RS232, RS3846, USB) have been used to communicate with instruments. These protocols tend to be more difficult to network.

Finally, it is noted that while the above discussion makes frequent reference to "light" as the propagated, scattered and collected medium, such use is not to be construed as limiting the invention to application in the visible portion of the electromagnetic spectrum. Rather, various embodiments of the invention may encompass any portion of the electromagnetic spectrum appropriate for a given application, including, but not limited to the ultraviolet, visible, and infrared portions of the electromagnetic spectrum, collimated or uncollimated.

The embodiments above are intended to be illustrative and not limiting. Although aspects of the present invention have been described with reference to particular embodiments, those skilled in the art will recognize that changes can be made in form and detail without departing from the spirit and scope of the invention.

Any incorporation by reference of or other reference to documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An instrument for measuring size segregated mass concentration of an aerosol, comprising:
   a first inlet for intake of an incoming aerosol flow stream containing incoming particles, the inlet including a first adjustable inlet portion that enables passage of selected particles of the incoming particles, the selected particles having a size range;
   a first chamber operably coupled to the adjustable inlet portion, the chamber for reception of an aerosol flow stream containing the selected particles and for reception of a first beam of electromagnetic radiation for intersection with the selected particles within the first chamber;
   a first detector in communication with the first chamber, the first detector for detection of electromagnetic radiation scattered as a result of the intersection in the chamber of the selected particles with the first beam of electromagnetic radiation, the first detector for delivery of a first detector output signal; a second detector in communication with the first chamber, the second detector for detection of electromagnetic radiation scattered as a result of the intersection in the chamber of the particles with the first beam of electromagnetic radiation, the second detector for delivery of second detector output signal representative of a second characteristic of the scattered electromagnetic radiation; and
   a control system in communication with the first detector, the control system for reception of the first detector output signal and for determination of a size-segregated mass concentration of the incoming aerosol flow stream based upon the first detector output signal and the size range of the selected particles.

2. The instrument of claim 1, wherein the first adjustable inlet portion includes an adjustable cut-size inlet sample conditioner.

3. The instrument of claim 2, wherein the adjustable cut-size inlet sample conditioner is selected from the group consisting of an adjustable impactor, an adjustable cyclone, and a fan with adjustable speed.

4. The instrument of claim 1, wherein the first detector output signal is representative of an intensity of the electromagnetic radiation scattered as a result of the intersection in the chamber.

5. The instrument of claim 1, wherein the first detector is selected from the group consisting of a photodiode and a photomultiplier tube.

6. The instrument of claim 1, wherein the control system includes an adjustable inlet portion controller for control of the adjustable inlet portion, including control of the size range of the selected particles.

7. The instrument of claim 1, wherein the control system includes a signal conditioner for receipt of the first detector output signal and output of a conditioned signal.

8. The instrument of claim 7, wherein the conditioned signal is proportional to an intensity of the electromagnetic radiation scattered.

9. The instrument of claim 1, further comprising a processor for the determination of a size-segregated mass concentration of the incoming aerosol flow stream based upon the first detector output signal and the size range of the selected particles.

10. The instrument of claim 1, wherein the control system includes an output device for display, storage, or transfer of data relating to the size-segregated mass concentration.

11. The instrument of claim 1, further comprising a filter at an exit of the chamber, the filter for capturing particles to be weighed to determine mass concentration.

12. An instrument for measuring size segregated mass concentration of an aerosol, comprising:
    a chamber for reception of an incoming aerosol flow stream containing particles and for reception of a beam of electromagnetic radiation for intersection with the particles within the chamber;
    a first detector in communication with the chamber, the first detector for detection of electromagnetic radiation scattered as a result of the intersection in the chamber of the particles with the beam of electromagnetic radiation, the first detector for delivery of a first detector output signal representative of a first characteristic of the scattered electromagnetic radiation;
    a second detector in communication with the chamber, the second detector for detection of electromagnetic radiation scattered as a result of the intersection in the chamber of the particles with the first beam of electromagnetic radiation, the second detector for delivery of a second detector output signal representative of a second characteristic of the scattered electromagnetic radiation; and
    a control system in communication with the first and second detectors, the control system for reception of the first and second detector output signals and for determination of a size-segregated mass concentration of the incoming aerosol flow stream based upon the first and the second detector output signals.

13. The instrument of claim 12, wherein the first characteristic is an intensity of scattered electromagnetic radiation.

14. The instrument of claim 12, wherein the first characteristic is a pulse height.

15. The instrument of claim 12, wherein the second characteristic is a pulse height.

16. The instrument of claim 12, wherein the second characteristic is a pulse width.

17. The instrument of claim 12, wherein the control system further includes a first signal conditioner adapted to condition the first detector output signal and a second signal conditioner adapted to condition the second detector output signal.

18. The instrument of claim 12, wherein the control system further includes a processor for determination of a size-segregated mass concentration of the incoming aerosol flow stream based upon the first and the second detector output signals.

19. The instrument of claim 12, wherein the control system is adapted to determine a pulse area based on a first characteristic of pulse height and a second characteristic of pulse width, thereby determining a particle size.

20. The instrument of claim 12, further comprising a third detector adapted to detect a third characteristic.

21. An instrument for measuring size segregated mass concentration of an aerosol, comprising:
- a first chamber for reception of a first portion of an incoming aerosol flow stream containing first particles and for reception of a first beam of electromagnetic radiation for intersection with the first particles within the first chamber;
- a second chamber for reception of a second portion of the incoming aerosol flow stream containing second particles and for reception of a second beam of electromagnetic radiation for intersection with the second particles within the second chamber;
- a first detector in communication with the first chamber, the first detector for detection of electromagnetic radiation scattered as a result of the intersection in the first chamber of the first particles with the first beam of electromagnetic radiation, the first detector for delivery of a first detector output signal representative of a first characteristic of the scattered electromagnetic radiation in the first chamber;
- a second detector in communication with the second chamber, the second detector for detection of electromagnetic radiation scattered as a result of the intersection in the second chamber of the second particles with the second beam of electromagnetic radiation, the second detector for delivery of a second detector output signal representative of a second characteristic of the scattered electromagnetic radiation in the second chamber; and
- a control system in communication with the first and second detectors, the control system for reception of the first and second detector output signals and for determination of a size-segregated mass concentration of the incoming aerosol flow stream based upon the first and the second detector output signals.

22. The instrument of claim 21, wherein the first characteristic is an intensity of scattered electromagnetic radiation.

23. The instrument of claim 21, wherein the second characteristic is a pulse height.

24. The instrument of claim 21, wherein the second characteristic is a pulse width.

25. The instrument of claim 21, wherein the control system further includes a first signal conditioner adapted to condition the first detector output signal and a second signal conditioner adapted to condition the second detector output signal.

26. The instrument of claim 21, wherein the control system further includes a processor for determination of a size-segregated mass concentration of the incoming aerosol flow stream based upon the first and the second detector output signals.

27. The instrument of claim 21, wherein the control system is adapted to determine a pulse area based on a first characteristic of pulse height and a second characteristic of pulse width, thereby determining a particle size.

28. An instrument for measuring size segregated mass concentration of an aerosol, comprising:
- a first inlet for intake of a first portion of an incoming aerosol flow stream containing incoming particles, the first inlet including a first adjustable inlet portion that enables passage of first selected particles of the incoming particles, the first selected particles having a first size range;
- a second inlet for intake of a second portion of the incoming aerosol flow stream containing incoming particles, the second inlet including a second adjustable inlet portion that enables passage of second selected particles of the incoming particles, the selected particles having a second size range;
- a first chamber operably coupled to the first adjustable inlet portion, the chamber for reception of an aerosol flow stream containing the first selected particles and for reception of a first beam of electromagnetic radiation for intersection with the first selected particles within the first chamber;
- a second chamber operably coupled to the second adjustable inlet portion, the second chamber for reception of an aerosol flow stream containing the second selected particles and for reception of a second beam of electromagnetic radiation for intersection with the second selected particles within the second chamber;
- a first detector in communication with the first chamber, the first detector for detection of electromagnetic radiation scattered as a result of the intersection in the first chamber of the first selected particles with the first beam of electromagnetic radiation, the first detector for delivery of a first detector output signal;
- a second detector in communication with the second chamber, the second detector for detection of electromagnetic radiation scattered as a result of the intersection in the chamber of the second selected particles with the second beam of electromagnetic radiation, the second detector for delivery of a second detector output signal; and
- a control system in communication with the first and second detectors, the control system for reception of the first and second detector output signals and for determination of a size-segregated mass concentration of the incoming aerosol flow stream based upon the first and the second detector output signals.

29. The instrument of claim 28, wherein the first detector output represents an intensity of scattered electromagnetic radiation in the first chamber due to the intersection of the first beam with the first selected particles having a first size range.

30. The instrument of claim 28, wherein the second detector output represents an intensity of scattered electromagnetic radiation in the second chamber due to the intersection of the second beam with the second selected particles having a second size range.

31. The instrument of claim 28, wherein the control system further includes a first signal conditioner adapted to condition the first detector output signal and a second signal conditioner adapted to condition the second detector output signal.

32. The instrument of claim 28, wherein the control system further includes a processor for determination of a size-segregated mass concentration of the incoming aerosol flow stream based upon the first and the second detector output signals.

33. An instrument for measuring size segregated mass concentration of an aerosol, comprising:
- a chamber for reception of an incoming aerosol flow stream containing particles and for reception of a first beam of electromagnetic radiation having a first wavelength and a second beam of electromagnetic radiation having a second fluorescence-inducing wavelength, the first and second beams for intersection with the particles within the first chamber;
- a first detector in communication with the chamber, the first detector for detection of electromagnetic radiation of the first wavelength scattered as a result of the intersection in the first chamber of the particles with the first beam of electromagnetic radiation, the first detector for delivery of a first detector output signal representative of a first characteristic of the scattered electromagnetic radiation;
- a second detector in communication with the chamber, the second detector operable at a bandwidth for detection of fluoresced electromagnetic radiation emitted by the particles after intersection with the second beam of electromagnetic radiation, the second detector for delivery of a second detector output signal representative of the fluoresced electromagnetic radiation; and a control system in communication with the first and second detectors, the control system for reception of the first and second detector output signals and for determination of a size-segregated mass concentration of the incoming aerosol flow stream based upon the first and the second detector output signals.

34. The instrument of claim 33, wherein the second detector includes optical filters in front of the second detector for detection of fluoresced electromagnetic radiation emitted by the particles after intersection with the second beam.

* * * * *